United States Patent
Rodriguez et al.

(10) Patent No.: US 7,067,686 B1
(45) Date of Patent: Jun. 27, 2006

(54) SYNTHESIS OF BENZYL-METAL COMPOUNDS

(75) Inventors: George Rodriguez, Houston, TX (US); David Arthur Cano, Spring, TX (US); David H. McConville, Houston, TX (US); Frank C. Rix, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 11/186,259

(22) Filed: Jul. 21, 2005

(51) Int. Cl.
*C07F 7/00* (2006.01)
*C07F 15/00* (2006.01)
*C07F 9/00* (2006.01)

(52) U.S. Cl. .................... 556/52; 556/43; 556/46; 556/58; 556/136; 556/140

(58) Field of Classification Search ................. 556/43, 556/46, 52, 58, 136, 140
See application file for complete search history.

(56) References Cited

U.S. PATENT DOCUMENTS

| 3,855,258 A | 12/1974 | Pioli | 260/429.3 |
| 3,933,876 A | 1/1976 | Tebbe | 260/429 |

OTHER PUBLICATIONS

Boustany et al., Helvetica Chimica Acta, vol. 50, No. 5, pp. 1305-1313 (1967).*
Jacob et al., Zeitschrift fur Anorganische Chemie, vol. 415, No. 2, pp. 109-114 (1975).*
Jacot-Guillarmod, Andre; Tabacchi, Raffaele; Porret, Jacques; "*Studies on organometallic compounds, VIII [1] Synthesis of tetrabenzyltitanium*" Helvetica Chimica Acta (1970), 53(6), pp. 1491-1494.
Felten, J.J.; Anderson, W.P., "*Nuclear Magnetic Resonance Studies of Lewis Base Adducts of Tetrabenzylhafnium and Tetrabenzylzirconium*" J. Organometal. Chem, (1972) 36.
Zucchini, U.; Albizzata E.; Giannini U.; *Synthesis and Properties of Some Titanium and Zirconium Benzyl Derivatives* J. Organometal. Chem., 26 (1971) 357-372.
Groysman, Stanislav; Goldberg, Israel; Kol, Moshe; Goldschmidt, Zeev; "*Pentabenzyltantalum: Straightforward Syntheses, X-ray Structure, and Application in the Synthesis of [O2N]TaBn3-Type and [O3N]TaBn2-Type Complexes*" Organometallics (2003), 22(19), pp. 3793-3795.
Razuvaev, G.A.; Latyaeva, V.N.; Vyshinskaya, L.I.; Lineva, A.N.; Drobotenko, V.V.; Cherkasov, V.K.; "*Some Reactions of tetrabenzylvanadium*" Journal of Organometallic Chemistry (1975), 93(1), pp. 113-118.
Razuvaev, G.A.; Latyaeva, V.N.; Vyshinskaya, L.I.; Drobotenko, V.V.; "*Synthesis and properties of covalent tri- and tetravalent vanadium*" Journal of Organometallic Chemistry (1981), 208(2), pp. 169-182.
Ibekwe, S.D.; Myatt, J.; "*Synthesis of ESR spectrum of tetrabenzylvanadium*" Journal of Organometallic Chemistry (1971), 31(3), C65-C67.
Tedesco, Consiglia; Immirzi, Attilio; Proto, Antonio; "*Structures of homoleptic benzyl derivatives of zirconium*" Acta Crystallographica, Section B: Structural Science (1998), B54(4), pp. 431-437.
Bacconsal, J.K.; Job, B.E.; O'Brien S.; "*Proton Magnetic Resonance and Mass Spectra of Some Isoleptic Transition-metal π-Allyl Complexes*" J. Chem. Soc. (A) (1967), 423-430.
Covert, Katharine J.; Mayol, Ana-Rita; Wolczanski, Peter T.; *Carbon-oxygen and related R-X bond cleavages mediated by (silox) 3Ti and other Group 4 derivatives (silox=tBu3SiO)* Inorganica Chimica Acta (1997), 263 (1-2), pp. 263-278.
Mowat, Walter; Shortland, Anthony J.; Hill, Nicholas J.; Wilkinson, Geoffrey; "*Elimination stabilized alkyls. II. Neopentyl and related alkyls of chromium(IV)*" Journal of the Chemical Society, Dalton Transactions: Inorganic Chemistry (1972-1999) (1973), (7), pp. 770-778.

* cited by examiner

*Primary Examiner*—Porfirio Nazario-Gonzalez
(74) *Attorney, Agent, or Firm*—Kevin M. Faulkner; Leandro Arechederra

(57) ABSTRACT

Disclosed are methods of producing di-, tri- or tetrabenzyl-metal compounds comprising combining a metal salt with a (benzyl)$_n$MgX$_{2-n}$ compound at from less than 30° C., wherein n is 1 or 2 and X is a monoanionic group; wherein the combining takes place in a diluent mixture comprising from 0 to 80% by volume of an ether diluent and a diluent selected from the group consisting of aromatic diluents, halogenated hydrocarbon diluents, and mixtures thereof. The methods are characterized by employing various mixtures of diluents, and in some cases, minimal to no ether diluent.

24 Claims, No Drawings

SYNTHESIS OF BENZYL-METAL COMPOUNDS

FIELD OF THE INVENTION

The present invention relates to methods of synthesizing organometallic compounds of, for example, Group 3 to Group 10 metals, and more particularly relates to synthesis of di-, tri- and tetra-benzyl compounds of Group 3 to Group 10 metals in other embodiments, most particularly to the synthesis of tetrabenzylzirconium and tetrabenzylhafnium-type of compounds.

BACKGROUND OF THE INVENTION

It is well known to use ethers as a primary or exclusive diluent in reactions involving Grignard-type reagents. In particular, J. J. Felten and W. P. Anderson in 36 J. ORGANOMETALLIC CHEM. 87–92 (1972), and U. Zucchini, E. Albizzati and U. Giannini in 26 J. ORGANOMETALLIC CHEM. 357 (1971) disclosed the production of tetrabenzyltitanium, and its zirconium and hafnium analogues, using a Grignard reagent in reaction with the chloride salt of the metals, the reaction taking place exclusively in ether as the diluent. However, the yields were at or below about 60%. Given the expense of such starting materials and the desire to simplify purification processes, what would be useful is a method of producing benzyl-metal compounds at a higher yield. The inventors have solved this and other problems as described herein.

SUMMARY OF THE INVENTION

One aspect of the invention is directed to a method of producing a di-, tri- or tetrabenzyl-metal compound comprising combining a metal salt with a Grignard-type compound, in particular, a (benzyl)$_n$MgX$_{2-n}$ compound, at from less than 30° C., wherein n is 1 or 2 and X is a monoanionic group; wherein the combining takes place in a diluent mixture comprising from 0 to 80% by volume of the diluent mixture of an ether diluent, substantially no ether diluent in one embodiment, and a diluent selected from the group consisting of aromatic diluents, halogenated hydrocarbon diluents, and mixtures thereof.

Another aspect of the invention is directed to a method of producing a di-, tri- or tetrabenzyl-metal compound comprising first combining a Group 4 metal salt with a ether diluent and a hydrocarbon, halogenated hydrocarbon or aromatic diluent to form a Group 4 metal adduct in a diluent mixture. This is followed by combining the Group 4 metal adduct with additional ether diluent and a (benzyl)$_n$MgX$_{2-n}$ compound at between −100 and 30° C., wherein n is 1 or 2 and X is a monoanionic group.

These aspects may be combined with various embodiments disclosed herein to describe the invention(s).

DETAILED DESCRIPTION OF THE INVENTION

As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press 81$^{st}$ ed. 2000).

One aspect of the invention is directed to a method of producing a di-, tri- or tetrabenzyl-metal compound comprising combining a metal salt with a (benzyl)$_n$MgX$_{2-n}$ compound, wherein n is 1 or 2 and X is a monoanionic group; wherein the combining takes place in a diluent mixture comprising from 0 or 1 or 2 or 3 or 4 or 5 to 60 or 70 or 80% by volume of the diluent mixture of an ether diluent and a diluent selected from the group consisting of aromatic diluents, halogenated hydrocarbon diluents, and mixtures thereof. As used herein, "benzyl" is the moiety C$_6$H$_5$CH$_2$— or substituted versions thereof, and the term "monoanionic" refers to any anionic chemical moiety known in the art capable of forming a bonding association with the magnesium, wherein in one embodiment the anionic moiety "X" is a halide, preferably chloride or bromide. In a preferred embodiment, the method of this aspect of the invention is directed to producing tetrabenzyl-metal compounds.

The "(benzyl)$_n$MgX$_{2-n}$" is a Grignard compound in a preferred embodiment. These compounds are well known in the art can be produced by various known means.

In its broadest sense, the "metal salt" is any compound comprising elements from Groups 3 to 13 and Lanthanide elements bound to counter-anionic moieties such as halides, hydrides, sulfates, sulfides, alkyls, alkoxys or carboxylates, most preferably halides. The metal salt is selected from the group consisting of Group 3 to Group 10 metal salts in a preferred embodiment, Group 4, 5 and 6 metal salts in yet a more preferred embodiment, and is a Group 4 metal salt in an even more preferred embodiment, and is a zirconium or hafnium containing salt in yet a more preferred embodiment. Non-limiting examples of such metal salts include zirconium tetrachloride and hafnium tetrachloride.

The benzyl moiety (and substituted versions thereof) is more particularly represented by the formula:

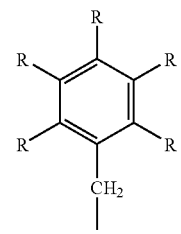

wherein each R is independently selected from hydride, halides, C$_1$ to C$_{10}$ alkyls, or C$_5$ to C$_{24}$ aryls; and wherein any two R groups can form a saturated or unsaturated ring.

In one embodiment of the method of producing the di-, tri- or tetrabenzyl-metal compound, the ether diluent is present from 1 to 80% by volume of the diluent mixture, and present from 20 to 80% by volume of the diluent mixture in a more preferred embodiment, and present from 30 to 70% by volume of the diluent mixture in a more preferred embodiment. The "ether diluent" can comprise any one or combination of ether compounds as is known in the art and is preferably a liquid at 1 atm. pressure and from −100 to 50° C. In a preferred embodiment, the ether diluent is selected from the group consisting of C$_2$ to C$_{10}$ ethers, C$_4$ to C$_{15}$ cyclic ethers, and mixtures thereof.

In a particular embodiment of this aspect of the invention, the ether diluent is substantially absent from the diluent mixture. By "substantially absent", what is meant is that ether diluent is not added to the diluent mixture, or may be present to less than 1% by volume of the diluent mixture as an impurity of the other diluents or as an impurity of the (benzyl)$_n$MgX$_{2-n}$ compound present to less than 1 wt % by weight of that compound.

The "diluent selected from the group consisting of aromatic diluents, halogenated hydrocarbon diluents, and mixtures thereof", or "aromatic and halogenated hydrocarbon diluents", make up the remaining portion of the diluent mixture; or in the case where an ether diluent is absent (or 0% by volume), an aromatic, halogenated hydrocarbon, or mixture thereof makes up the diluent mixture. In one embodiment, the diluent mixture is made up of from 30 to 80% by volume of an aromatic diluent, a halogenated hydrocarbon diluent, or some mixture thereof. The aromatic and halogenated hydrocarbon diluents are selected from the group consisting of $C_5$ to $C_{30}$ aromatics, $C_1$ to $C_{10}$ halogenated hydrocarbons, and mixtures thereof in one embodiment; more preferably, the aromatic and halogenated hydrocarbon diluents are selected from the group consisting of $C_6$ to $C_{12}$ aromatics, $C_1$ to $C_5$ halogenated hydrocarbons, and mixtures thereof; most preferably, the "diluent mixture" is an aromatic diluent selected from the group consisting of $C_6$ to $C_{12}$ aromatics. Examples of suitable halogenated hydrocarbons include methylene chloride, dichloroethane, trichloromethane, chloroethane, dichlorobutane, or mixtures thereof. Examples of suitable aromatics include benzene, toluene, xylene, and other alkyl-substituted aromatic compound.

The "combining" can take place by any suitable means known to those in the arts such as in various reaction vessels having a variety of geometries, and employing various means of agitation such as mechanical stirring, etc. In one embodiment, the combining takes place at from less than at from less than 30° C., and at from less than –30° C. in a more preferred embodiment. In certain embodiments, the combining may take place at from –100 to –30° C.; in other embodiments, especially when the metal salt is a hafnium salt, the combining may take place at from –30 to 30° C. in one embodiment.

The "combining" step results in a reaction product, preferably comprising mostly the desired benzyl-metal compound. The reaction product can be isolated and purified by means common in the art. In one embodiment, the product resulting from the combining step is isolated and extracted with a halogenated hydrocarbon, most preferably a $C_1$ to $C_5$ halogenated hydrocarbon. Further, the metal salt and the $(benzyl)_n MgX_{2-n}$ are combined in any desirable portion depending on the identity of both compounds and the desired product, preferably, the $(benzyl)_n MgX_{2-n}$ compound is added such that the number of "benzyl" equivalents is nearly the same as the number of monoanionic groups comprising the metal salt.

A preferred embodiment of the invention is a method of producing a di-, tri- or tetrabenzyl-metal compound, most preferably tetrabenzyl-metal compound, comprising combining a metal salt with a $(benzyl)_n MgX_{2-n}$ compound; wherein the combining takes place in a diluent comprising a mixture of an ether diluent and a diluent selected from the group consisting of hydrocarbon diluents, halogenated hydrocarbon diluents, and mixtures thereof. Most preferably, the ether diluent is present from 20 to 80% by volume of the diluent.

Another aspect of the invention is directed to a method of producing a di-, tri- or tetrabenzyl-metal compound comprising two steps:
(a) first combining the metal salt with a hydrocarbon diluent, halogenated hydrocarbon diluent, aromatic diluent or mixture thereof to form a Group 4 metal adduct in a first diluent mixture;

(b) combining the Group 4 metal adduct with the $(benzyl)_n MgX_{2-n}$ compound forming a second diluent mixture.

wherein in one embodiment of step (a) an ether diluent is also present; and wherein in another embodiment of step (a) the ether diluent is present from 1 to 40% by volume of the first diluent mixture; and wherein in another embodiment of step (b) an ether diluent is also present; and wherein in yet another embodiment of step (b) the ether diluent is from 30 to 80% by volume of the second diluent mixture.

In one embodiment, the combining in the second step takes place at from at between –100 or –90 or –80 and –30 or 20 or 30 or 40° C. The "diluents" referred to here have the same meaning as in the first aspect of the invention, as do the other terms. The "hydrocarbon diluent" is any hydrocarbon known in the art that is preferably a liquid at from –100 to 10 or 26 or 40° C., examples of which include pentane, hexane, cyclohexane, mineral oils, decalin, naphthas, and other known hydrocarbons. In one embodiment, the hydrocarbon diluent is selected from the group consisting of $C_1$ to $C_{12}$ non-cyclic hydrocarbons and $C_4$ to $C_9$ cyclic hydrocarbons, and more preferably selected from the group consisting of $C_3$ to $C_{10}$ non-cyclic hydrocarbons.

In the second step of this aspect of the invention, the $(benzyl)_n MgX_{2-n}$ is a solid, or is in a diluent selected from the group consisting of ether diluents, hydrocarbon diluents, aromatic diluents, halogenated hydrocarbon diluents, and mixtures thereof. In one embodiment of the second step, the $(benzyl)_n MgX_{2-n}$ is solid, or in a diluent selected from the group consisting of hydrocarbon diluents, aromatic diluents, halogenated hydrocarbon diluents, and mixtures thereof.

Preferably in the first step, the ether diluent is present from 1 to 40% by volume of the first diluent mixture, and present from 6 to 20% by volume of the first diluent mixture in a more preferred embodiment. Preferably in the second or subsequent step the total amount of ether diluent present in the second diluent mixture is from 30 to 80% by volume of the total diluent mixture, and most preferably present from 40 to 70% by volume of the second diluent mixture. Most preferably, the Group 4 metal salt is a zirconium or hafnium tetrahalide compound.

In a particular embodiment of this aspect of the invention, the ether diluent is substantially absent from the diluent mixture in the first, second, or both steps. By "substantially absent", what is meant is that ether diluent is not added to the diluent mixture, or may be present to less than 1% by volume of the diluent mixture as an impurity of the other diluents or as an impurity of the $(benzyl)_n MgX_{2-n}$ compound present to less than 1 wt % by weight of that compound. Thus, in one embodiment, the first or second diluent mixtures consist of any one or mixture of a hydrocarbon diluent, aromatic diluent or halogenated hydrocarbon diluent.

A preferred embodiment of this aspect of the invention is a method of producing a di-, tri- or tetrabenzyl-metal compound, most preferably tetrabenzyl-metal compound, comprising
(a) first combining a Group 4 metal salt with an ether diluent and a hydrocarbon, halogenated hydrocarbon or aromatic diluent to form a Group 4 metal adduct;
(b) combining the Group 4 metal adduct with additional ether diluent and a $(benzyl)_n MgX_{2-n}$ compound at between –100 and 30° C.

In one embodiment, the method of the invention can be described more particularly, where an amount of diethyl ether ($Et_2O$) is added to a slurry of the metal salt zirconium tetrachloride in toluene such that the amount of ether is from 8 or 10 to 16 or 20% by volume of diluent mixture. The mixture is then cooled to from −50 to −80° C. Next, four equivalents of a (benzyl)$_n$MgX$_{2-n}$ compound, such as C$_6$H$_5$CH$_2$MgBr, are added to the mixture/adduct of the first step. The resulting slurry is then agitated for from 30 min to one to ten hours, depending upon the scale and other conditions. The solids can then be removed such as by gravity filtration. The solvents can then be at least partially removed under vacuum. Other diluents such as pentane can be added to induce further precipitation. The resulting slurry can then be chilled to −20 to 45° C. for an hour to several hours. The solid that results can then be collected by filtration and washed with a minimum amount of a hydrocarbon solvent such as hexane or pentane. This product can then be extracted, in one embodiment with a halogenated hydrocarbon, an example of which is methylene chloride (CH$_2$Cl$_2$). The filtrate can then be at least partially evaporated under vacuum. A hydrocarbon such as pentane or hexane can then be added to induce further precipitation, and or chilled. This procedure can afford a 65 to 90% yield of tetrabenzyl zirconium product. Common means such as proton NMR can be used to characterize the product.

In yet another particular embodiment, the metal salt hafnium tetrachloride is slurried in a halogenated hydrocarbon such as methylene chloride or an aromatic diluent such as toluene. The adduct mixture can then be chilled to from 0 to −30° C. Four equivalents of the (benzyl)$_n$MgX$_{2-n}$ compound such as C$_6$H$_5$CH$_2$MgBr in ether are then added to the mixture. The resulting slurry can then be stirred for 30 min to several hours at this temperature. The solids can then be collected by filtration, and the filtrate evaporated. The resulting product can then be washed with a minimum amount of a hydrocarbon such as hexane or pentane. This procedure can afford from 62 to 90% yield of tetrabenzyl hafnium product.

In yet another particular embodiment, diethyl ether is added to a slurry of zirconium tetrachloride in toluene such that the ether makes up about 15 or 20 to 40 or 45% by volume of the diluent mixture. The mixture is chilled to from −40 to −70° C. Next, four equivalents of a (benzyl)$_n$MgX$_{2-n}$ compound such as C$_6$H$_5$CH$_2$MgBr are added to the mixture. The resulting slurry is then stirred for 30 min to several hours. The diluents can then be at least partially removed under vacuum, and the solids removed by, for example, gravity filtration. A hydrocarbon such as pentane can be added to induce further precipitation. The resulting slurry can then be chilled to −40 to −25° C. The solid can then be collected by filtration and washed with minimum hydrocarbon solvent. This procedure affords from 65 to 95% yield of tetrabenzyl zirconium.

In yet another particular embodiment, the (benzyl)$_n$MgX$_{2-n}$ compound is suspended in a halogenated hydrocarbon diluent comprising substantially no ether diluent (0%) or 1 or 2 to 10% by volume of an ether diluent to form an adduct, and this mixture is used in combining with the metal salt. To effectuate this in one embodiment, an aliquot of the (benzyl)$_n$MgX$_{2-n}$ compound solution/slurry in diethylether is treated under vacuum to remove the ether. Other methods may also be used to remove the ether diluent known in the art such as, for example, heating combined with lower pressure, crystallization, etc. The residual viscous (benzyl)$_n$MgX$_{2-n}$ compound material is then redissolved in an amount of a halogenated hydrocarbon such as methylene chloride in one embodiment, or an aromatic diluent in another embodiment. The solution is then preferably chilled to from −40 to −80° C. This is followed by the addition of a slurry of the metal salt such as zirconium tetrachloride in a halogenated hydrocarbon, hydrocarbon, or aromatic diluent. This procedure can afford an overall yield of from 40% or more yield of the tetrabenzyl zirconium. The amount of ether diluent and/or the identity of the diluent used to suspend the Grignard may be modified to increase the overall yield of the tetrabenzyl-metal compound.

Another aspect of the invention relates to a method to prepare a metal compound comprising reacting a neutral ligand with the di-, tri- or tetrabenzyl metal compound in a non-coordinating or weakly coordinating solvent, at about 20° C. or above, preferably at about 20 to about 100° C., then treating the mixture with an excess of an alkylating agent, then recovering the metal complex. In a preferred embodiment the solvent has a boiling point above 60° C., such as ether, toluene, xylene, benzene, methylene chloride and/or hexane. Such syntheses are also described in, for example, U.S. Pat. No. 5,576,460, U.S. Pat. No. 6,518,444 and U.S. Pat. No. 6,855,839, and references cited therein.

In a preferred embodiment the neutral ligand is represented by the formula:

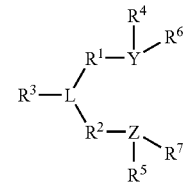

wherein Y is a group 15 element, preferably nitrogen or phosphorus;
Z is a group 15 element, preferably nitrogen or phosphorus;
L is a group 15 or 16 element, preferably nitrogen;
$R^1$ and $R^2$ are independently a $C_1$ to $C_{20}$ hydrocarbylene group or a $C_1$ to $C_{20}$ a heteroatom containing hydrocarbylene group, where the heteroatom is selected from silicon, germanium, tin, lead, and phosphorus;
$R^1$ and $R^2$ may also be interconnected to each other;
$R^3$ is absent, or is hydrogen, a group 14 atom containing group, a halogen, a heteroatom containing group;
$R^4$ and $R^5$ are independently an aryl group, a substituted aryl group, a cyclic alkyl group, a substituted cyclic alkyl group, or multiple ring system;
$R^6$ and $R^7$ are independently absent or hydrogen, halogen, a heteroatom (esp. Si, N, Al, B, O, S; and having its valency satisfied with a hydride, halide or a $C_1$ to $C_{20}$ hydrocarbon), a hydrocarbyl group, or a heteroatom containing group.

The invention also relates to the use of a metal compound, preferably a catalyst compound useful in producing polyolefins, made by the process comprising reacting a neutral ligand with the di-, tri- or tetrabenzyl metal compound; wherein the di-, tri- or tetrabenzyl metal compound is made by combining a metal salt with a (benzyl)$_n$MgX$_{2-n}$ compound, wherein n is 1 or 2 and X is a monoanionic group; wherein the combining takes place in a diluent mixture comprising an ether diluent and a diluent selected from the group consisting of aromatic diluents, halogenated hydrocarbon diluents, and mixtures thereof. This aspect of the invention can be combined with embodiments of other aspects of the invention as described herein. For example, the di-, tri- or tetrabenzyl metal compound may also be made by the process of:
(a) first combining a Group 4 metal salt with a hydrocarbon, halogenated hydrocarbon, aromatic diluent or mixture thereof, and optionally an ether diluent, to form a Group 4 metal adduct in a first diluent mixture;

(b) combining the Group 4 metal adduct with a (benzyl)$_n$MgX$_{2-n}$ compound, and optionally additional ether diluent forming a second diluent mixture.

The benzyl-metal compounds are useful in a number of applications, including the further synthesis of metal compounds such as {[(phenyl)NCH$_2$CH$_2$]$_2$NH}Zr(CH$_2$C$_6$H$_5$)$_2$, {[(pentamethyl-phenyl)NCH$_2$CH$_2$]$_2$NH}Zr(CH$_2$C$_6$H$_5$)$_2$, {[(pentamethyl-phenyl)NCH$_2$CH$_2$]$_2$NH}Hf(CH$_2$C$_6$H$_5$)$_2$, {[(pentamethyl-phenyl)NCH$_2$CH$_2$]$_2$NH}Ti(CH$_2$C$_6$H$_5$)$_2$, and other such compounds. These compounds are useful olefin polymerization catalysts and are disclosed in, for example, U.S. Pat. No. 6,608,149 and U.S. Pat. No. 6,281,306.

Thus, the compositions and methods of the present invention can be described alternately by any of the embodiments disclosed herein, or a combination of any of the embodiments described herein. Embodiments of the invention, while not meant to be limiting by, may be better understood by reference to the following examples.

EXAMPLES

Example 1

To a slurry of ZrCl$_4$ (1.000 gram) in CH$_2$Cl$_2$ (10.0 ml) was added Et$_2$O (10.0 ml). The mixture was chilled to −70° C. Four equivalents of C$_6$H$_5$CH$_2$MgBr (1M in Et$_2$O, Aldrich) were added to the mixture. The resulting yellow slurry was stirred for 3 hour. The solvents were replaced with CH$_2$Cl$_2$, and the solids removed by filtration using vacuum to pull the filtrate through. A small amount of precipitate was present in the filtrate. No efforts were made to quantify these solids. Example 2 below shows one way to remove these solids. The volume of the filtrate was reduced by approximately 98–99%. Pentane was added to induce further precipitation. The resulting slurry was chilled to −35° C. for 1 hour. The orange solid was collected by filtration and washed with minimum pentane. The solids were placed under vacuum for 2 hours. This procedure afforded 1.524 grams (78%) of product. Proton NMR spectroscopy was used to characterize the product.

Example 2

A portion of the product obtained in Example 1 was placed in CHCl$_3$. The resulting mixture was cloudy. The solids were removed by filtration. The filtrate was evaporated to leave an orange solid product. This indicates that a second filtration may be necessary to remove residual magnesium salts. An alternative approach is to induce precipitation of the salts using 1,4-dioxane (see below).

Example 3

The procedure described in Example 2 was used, except that a mixture 20 mls of Et$_2$O and 1.5 mls 1,4-dioxane was used for the extraction. This step helps to remove residual Mg salts. This procedure afforded 0.857 grams of product (44%). This low yield may be due to difficulties with the filtration.

Comparative Example 4

To a mixture of ZrCl$_4$ (3.101 grams) in Et$_2$O (30 ml) chilled at −60° C. was added 4 equivalents of C$_6$H$_5$CH$_2$MgBr (54 ml in Et$_2$O, 1M, Aldrich). The resulting yellow slurry was stirred for 2 hour. The solvent was removed by evaporation and replaced with CHCl$_3$, and the resulting solids removed by filtration using vacuum to pull the filtrate through. The volume of the filtrate was reduced by approximately 90%. Pentane was added to induce further precipitation. The resulting slurry was chilled to −35° C. for 1 hour. The orange solid was collected by filtration and washed with a minimum amount of pentane. The solids were placed under vacuum for 2 hours. This procedure afforded 3.520 grams of product (58%). Proton NMR spectroscopy was used to characterize the product.

Example 5

To a slurry of ZrCl$_4$ (2.901 grams) in CH$_2$Cl$_2$ (15 ml) was added Et$_2$O (10.0 ml). The mixture was chilled to −70° C. Four equivalents of C$_6$H$_5$CH$_2$MgBr (1M in Et$_2$O, Aldrich) were added to the mixture. The resulting yellow slurry was stirred for two hour. The solvents were replaced with approximately 55 mls of CHCl$_3$, and the solids removed by filtration using vacuum to pull the filtrate through. The volume of the filtrate was reduced by approximately 90%. Pentane was added to induce further precipitation. The resulting slurry was chilled to −35° C. for 2 hour. The orange solid was collected by filtration and washed with a minimum amount of pentane. The solids were placed under vacuum for 2 hours. This procedure resulted in 4.135 grams (73%). Proton NMR spectroscopy was used to characterize the product.

Example 6

This example was similar to that described in Example 5. To a slurry of ZrCl$_4$ (2.320 grams) in CH$_2$Cl$_2$ (15.0 ml) was added Et$_2$O (8.0 ml). The mixture was chilled to −70° C. Four equivalents of C$_6$H$_5$CH$_2$MgBr (1M in Et$_2$O, Aldrich) were added to the mixture. The resulting yellow slurry was stirred for 2 hour. The solvents were replaced with CH$_2$Cl$_2$, and the solids removed by gravity filtration (not using vacuum to pull the filtrate through). The volume of the filtrate was reduced by approximately 90%. Pentane was added to induce further precipitation. The resulting slurry was chilled to −35° C. for 2 hour. The orange solid was collected by filtration and washed with minimum pentane. The solids were placed under vacuum for 2 hours. This procedure afforded 3.239 grams of product (72%). Proton NMR was used to characterize the product.

Example 7

To a slurry of ZrCl$_4$ (2.900 grams) in toluene (10.0 ml) was added Et$_2$O (5.0 ml). The mixture was chilled to −70° C. Four equivalents of C$_6$H$_5$CH$_2$MgBr (1M in Et$_2$O, Aldrich) were added to the mixture. The resulting yellow slurry was stirred for one hour. The solvents were partially removed under vacuum (90% removal), and the solids removed (gravity filtration). A small amount of precipitate was present in the filtrate. No efforts were made to quantify these solids. Example 3 shows one way to remove these solids. The volume of the filtrate was reduced by approximately 90%. Pentane was added to induce further precipitation. The resulting slurry was chilled to −35° C. for 1 hour. The orange solid was collected by filtration and washed with minimum pentane. The solids were placed under vacuum for 2 hours. This procedure afforded 4.878 grams of product (86%). Proton NMR was used to characterize the product.

Example 8

To a slurry of ZrCl$_4$ (29.0 grams) in toluene (300 ml) was added Et$_2$O (50 ml). The mixture was chilled to −70° C. Four equivalents of C$_6$H$_5$CH$_2$MgBr (1M in Et$_2$O, Aldrich) were added to the mixture. The resulting yellow slurry was stirred for one hour. The solids removed (gravity filtration). The solvents were partially removed under vacuum (approximately 90% removal). The filtrate showed some cloudiness. No efforts to quantify these solids were made. Example 3 shows one way to remove these solids. The volume of the filtrate was reduced by approximately 90%. Pentane was added to induce further precipitation. The resulting slurry was chilled to −35° C. for 1 hour. The orange solid was collected by filtration and washed with a minimum amount of pentane. This product was extracted with CH$_2$Cl$_2$. The filtrate was partially evaporated under vacuum (approximately 90% removal). Pentane was added to induce further precipitation. The resulting slurry was chilled to −35° C. for 1 hour. The orange solid was collected by filtration and washed with a minimum amount of pentane. The solids were placed under vacuum for 2 hours. This procedure afforded 43.225 grams of product (76%). Proton NMR was used to characterize the product.

Example 9

A slurry of ZrCl$_4$ (1.399 grams) in toluene (20 ml) was chilled to 60° C. To this slurry was added 4.067 grams of (C$_6$H$_5$CH$_2$)$_2$Mg(1,4-dioxane)$_{1.5}$ (solid) all at once. After stirring for 30 minutes at −60° C., then 10 mls of 1.4-dioxane were added. The mixture was allowed to reach room temperature over 2 hours. The solids were collected and washed with 10 mls of toluene. The filtrate was evaporated leaving an orange semisolid. Pentane was added to the resulting orange solids, and the product was collected by filtration. After drying under vacuum 2.139 grams of product were obtained. The solid obtained after the first filtration was extracted further with 50 mls of CH$_2$Cl$_2$. The second filtrate was worked-up as described above, and afforded an additional 1.869 grams. This procedure resulted in a total yield of 68%. Proton NMR was used to characterize the product.

Example 10

A slurry of ZrCl$_4$ (10 grams) in toluene (100 ml) was chilled to −70° C. Four equivalents of C$_6$H$_5$CH$_2$MgBr (175 ml, 1M in Et$_2$O, Aldrich) were added to the mixture. The resulting yellow slurry was stirred for one hour. The solvents were partially removed under vacuum, and the solids removed (gravity filtration). A small amount of precipitate was present in the filtrate. Five milliliters of anhydrous 1,4-dioxane were added to induce further precipitation of magnesium salts. The mixture was filtered again. The resulting clear, orange solution was evaporated to approximately 10% of the initial volume. The product precipitates half way through the evaporation. To this mixture was added 20 ml of anhydrous pentane to further induce product precipitation. The flask was chilled to −35° C. for 1 hour. The product collected and washed with a minimum amount of cold pentane. This procedure resulted in an orange, crystalline solid (13.253 grams, 68%). Proton NMR was used to characterize the product.

Example 11

HfCl$_4$ (2.000 gram) was slurried in CH$_2$Cl$_2$ (10.0 ml). The mixture was chilled to −70° C. Four equivalents of C$_6$H$_5$CH$_2$MgBr (1M in Et$_2$O, Aldrich) were added to the mixture. The resulting yellow slurry was stirred for 5 hour. The mixture was allowed to reach room temperature and stirred over night (total of approximately 18 hours). The solids were collected by filtration. The filtrate was evaporated. The resulting orange product was washed with a minimum amount of pentane. The solids were placed under vacuum for 2 hours. This procedure afforded 2.256 grams (66.5%) of product. Proton NMR spectroscopy was used to characterize the product.

Example 12

HfCl$_4$ (2.000 gram) was slurried in CH$_2$Cl$_2$ (10.0 ml). The mixture was chilled to −20° C. Four equivalents of C$_6$H$_5$CH$_2$MgBr (1M in Et$_2$O, Aldrich) were added to the mixture. The resulting yellow slurry was stirred for 3 hour. The solids were collected by filtration. The filtrate was evaporated. The resulting orange product was washed with a minimum amount of pentane. The solids were placed under vacuum for 2 hours. This procedure afforded 2.351 grams (69.3%) of product. Proton NMR spectroscopy was used to characterize the product.

Example 13

To a slurry of HfCl$_4$ (64.056 grams) in toluene (300 ml) was added Et$_2$O (100.0 ml). Four equivalents of C$_6$H$_5$CH$_2$MgBr (800 mls, 1M in Et$_2$O, Aldrich) were added to the mixture. The resulting yellow slurry was stirred for two hour. The solids were allowed to settle, then were collected by filtration. To the filtrate was added approximately 10 mls of 1,4-dioxane to precipitate any residual magnesium salts. The solids were removed by filtration. The volume of the filtrate was reduced by approximately 90%. Pentane was added to induce further precipitation. The resulting slurry was chilled to −35° C. for 2 hour. The orange solid was collected by filtration and washed with a minimum amount of pentane. The solids were placed under vacuum for 2 hours. This procedure resulted in 66.244 grams (60.9%). Proton NMR spectroscopy was used to characterize the product.

Example 14

Most of the solvent from a 150.0 milliliter aliquot of a 1M C$_6$H$_5$CH$_2$MgBr solution in Et$_2$O was removed under vacuum. The residual viscous material was redissolved in 150 of CH$_2$Cl$_2$. The solution was chilled to −70° C. To this solution was added a slurry of ZrCl4 (8.739 gram) in CH$_2$Cl$_2$ (20.0 ml). The resulting yellow slurry was stirred for 1.5 hour. The solids were removed by filtration using vacuum to pull the filtrate through. A small amount of precipitate was present in the filtrate. Approximately 6 milliliters of 1,4-dioxane were added to the filtrate. More solids precipitated. These solids were removed by filtration. The volume of the filtrate was reduced by approximately 80%. Pentane was added to induce further precipitation. The resulting slurry was chilled to −35° C. for 1 hour. The orange solid was collected by filtration and washed with minimum pentane. The solids were placed under vacuum for 2 hours. This procedure afforded 7.521 grams (44%) of product. Proton NMR spectroscopy was used to characterized the product.

TABLE 1

Yields of Reactions

| Example No. | Yield (%), Zr/HfBz$_4$ | Description |
|---|---|---|
| 1 | 78 | Reaction in CH$_2$Cl$_2$/Et$_2$O then extract with CH$_2$Cl$_2$ (some cloudiness in filtrate) |
| 2 | n.m. | A portion of product from Ex. 1 was extracted with CHCl$_3$ |
| 3 | 44 | Reaction in CH$_2$Cl$_2$/Et$_2$O, then extract with Et$_2$O/1,4-dioxane |
| 4 | 58 | Reaction in Et$_2$O, then extract with CHCl$_3$ |
| 5 | 73 | Reaction in CH$_2$Cl$_2$/Et$_2$O, then extract with CHCl$_3$ |
| 6 | 72 | Reaction in CH$_2$Cl$_2$/Et$_2$O then extract with CH$_2$Cl$_2$ (no cloudiness in filtrate) |
| 7 | 86 | Reaction in toluene/Et$_2$O |
| 8 | 76 | Reaction in toluene/Et$_2$O, then extract with CH$_2$Cl$_2$ |
| 9 | 68 | Reaction in toluene using dibenzylmagnesium |
| 10 | 67 | Reaction in toluene. |
| 11 | 67 | Tetrabenzylhafnium made in CH$_2$Cl$_2$. |
| 12 | 69 | Tetrabenzylhafnium made in CH$_2$Cl$_2$ at −20° C. |
| 13 | 61 | Tetrabenzylhafnium made in CH$_2$Cl$_2$ at 23° C. |
| 14 | 44 | Removal of most Et$_2$O prior to combining step. | n.m. = not measured

We claim:

1. A method of producing a di-, tri- or tetrabenzyl-metal compound comprising combining a metal salt with a (benzyl)$_n$MgX$_{2-n}$ compound, wherein n is 1 or 2 and X is a monoanionic group; wherein the combining takes place in a diluent mixture comprising from 0 to 80% by volume of the diluent mixture of an ether diluent, and a diluent selected from the group consisting of aromatic diluents, halogenated hydrocarbon diluents, and mixtures thereof.

2. The method of claim 1, wherein the metal salt is selected from the group consisting of Group 3 to Group 10 metal salts.

3. The method of claim 1, wherein the metal salt is a Group 4 metal salt.

4. The method of claim 1, the metal salt is a zirconium or hafnium containing salt.

5. The method of claim 1, wherein the benzyl moiety is represented by the formula:

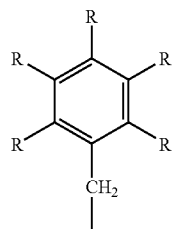

wherein each R is independently selected from hydride, halides, C$_1$ to C$_{10}$ alkyls, or C$_5$ to C$_{24}$ aryls, wherein any two R groups can form a saturated or unsaturated ring.

6. The method of claim 1, wherein the ether diluent is substantially absent from the diluent mixture.

7. The method of claim 1, wherein the ether diluent is present from 1 to 80% by volume of the diluent mixture.

8. The method of claim 1, wherein the ether diluent is present from 30 to 70% by volume of the diluent mixture.

9. The method of claim 1, wherein the ether diluent is selected from the group consisting if C$_2$ to C$_{10}$ ethers, C$_4$ to C$_{15}$ cyclic ethers, and mixtures thereof.

10. The method of claim 1, wherein the aromatic and halogenated hydrocarbon diluents are selected from the group consisting of C$_5$ to C$_{30}$ aromatics, C$_1$ to C$_{10}$ halogenated hydrocarbons, and mixtures thereof.

11. The method of claim 1, wherein the aromatic and halogenated hydrocarbon diluents are selected from the group consisting of C$_6$ to C$_{12}$ aromatics, C$_1$ to C$_5$ halogenated hydrocarbons, and mixtures thereof.

12. The method of claim 1, wherein the aromatic and halogenated hydrocarbon diluents are selected from the group consisting of C$_6$ to C$_{12}$ aromatics.

13. The method of claim 1, wherein the combining takes place at from less than −30° C.

14. The method of claim 1, wherein the product resulting from the combining step is isolated and extracted with a halogenated hydrocarbon.

15. The method of claim 1, wherein the combining takes place by:
(a) first combining the metal salt with a hydrocarbon diluent, halogenated hydrocarbon diluent, aromatic diluent or mixture thereof to form a Group 4 metal adduct in a first diluent mixture;
(b) combining the Group 4 metal adduct with the (benzyl)$_n$MgX$_{2-n}$ compound forming a second diluent mixture.

16. The method of claim 15, wherein in step (a) an ether diluent is also present.

17. The method of claim 16, wherein in step (a) the ether diluent is present from 1 to 40% by volume of the first diluent mixture.

18. The method of claim 15, wherein in step (b) an ether diluent is also present.

19. The method of claim 18, wherein in step (b) the ether diluent is from 30 to 80% by volume of the second diluent mixture.

20. The method of claim 15, wherein the hydrocarbon, halogenated hydrocarbon or aromatic diluent is selected from the group consisting of C$_4$ to C$_{16}$ hydrocarbons, C$_1$ to C$_{10}$ halogenated hydrocarbons, and mixtures thereof.

21. The method of claim 15, wherein the hydrocarbon, halogenated hydrocarbon or aromatic diluent is selected from the group consisting of C$_4$ to C$_{16}$ alkanes, C$_6$ to C$_{12}$ aromatics, C$_1$ to C$_5$ halogenated hydrocarbons, and mixtures thereof.

22. The method of claim 15, wherein the hydrocarbon, halogenated hydrocarbon or aromatic diluent is selected from the group consisting of C$_6$ to C$_{12}$ aromatics.

23. The method of claim 15, wherein the combining in step (b) takes place at between −100 and 40° C.

24. A method of preparing a metal compound comprising reacting a neutral ligand with the di-, tri- or tetrabenzyl metal compound; wherein the di-, tri- or tetrabenzyl metal compound is made by combining a metal salt with a (benzyl)$_n$MgX$_{2-n}$ compound, wherein n is 1 or 2 and X is a monoanionic group; wherein the combining takes place in a diluent mixture comprising from 0 to 80% by volume of an ether diluent and a diluent selected from the group consisting of aromatic diluents, halogenated hydrocarbon diluents, and mixtures thereof.

* * * * *